United States Patent
Cooke et al.

(10) Patent No.: US 10,260,181 B2
(45) Date of Patent: Apr. 16, 2019

(54) DIRECTIONAL MESH AND ASSOCIATED SYSTEMS

(71) Applicant: Lake Region Medical, Inc., Chaska, MN (US)

(72) Inventors: David S. Cooke, Harvard, MA (US); Scott T. Latterell, Hermosa Beach, CA (US)

(73) Assignees: Lake Region Medical, Inc., Wilmington, MA (US); Scott T. Latterell, Hermosa Beach, CA (US)

( * ) Notice: Subject to any disclaimer, the term of this patent is extended or adjusted under 35 U.S.C. 154(b) by 368 days.

(21) Appl. No.: 14/155,233

(22) Filed: Jan. 14, 2014

(65) Prior Publication Data

US 2014/0200579 A1  Jul. 17, 2014

Related U.S. Application Data

(60) Provisional application No. 61/752,314, filed on Jan. 14, 2013.

(51) Int. Cl.
| | | |
|---|---|---|
| *A61B 18/14* | (2006.01) | |
| *D04C 1/06* | (2006.01) | |
| *A61B 18/00* | (2006.01) | |
| *D04C 1/02* | (2006.01) | |
| *D04C 3/40* | (2006.01) | |

(52) U.S. Cl.
CPC .............. *D04C 1/02* (2013.01); *A61B 18/14* (2013.01); *D04C 1/06* (2013.01); *D04C 3/40* (2013.01); *A61B 2018/00267* (2013.01)

(58) Field of Classification Search
CPC ........ B29C 53/587; A61B 2018/00077; A61B 2018/00267; A61B 2018/1465; A61B 2018/1435; A61B 2018/1437
See application file for complete search history.

(56) References Cited

U.S. PATENT DOCUMENTS

| | | | | |
|---|---|---|---|---|
| 4,630,611 A | * | 12/1986 | King ...................... | A61B 5/076 600/377 |
| 4,840,186 A | * | 6/1989 | Lekholm ................ | A61N 1/056 607/116 |
| 5,334,169 A | * | 8/1994 | Brown ............... | A61M 25/0023 604/265 |
| 5,524,619 A | * | 6/1996 | Ouchi .................. | A61B 5/0422 600/373 |
| 5,549,109 A | * | 8/1996 | Samson ............... | A61B 5/6851 600/381 |
| 5,797,905 A | * | 8/1998 | Fleischman .......... | A61B 5/0422 374/E1.005 |

(Continued)

*Primary Examiner* — Ronald Hupczey, Jr.
(74) *Attorney, Agent, or Firm* — Michael F. Scalise; Ganz Law, P.C.

(57) ABSTRACT

Woven structures and associated systems for weaving such structures are disclosed. Some disclosed innovations pertain to braided structures, such as braided wire structures, with axially asymmetric woven structures (or "directional meshes") being examples. Other innovations disclosed herein pertain to methods of manufacturing woven structures, with automated methods of braiding directional meshes being examples. Some directional mesh embodiments can be configured and used as energizable electrodes for electrosurgical therapies, for example, bipolar vaporization therapies.

23 Claims, 6 Drawing Sheets

(56) References Cited

U.S. PATENT DOCUMENTS

| | | | | |
|---|---|---|---|---|
| 5,810,887 A * | 9/1998 | Accorti, Jr. | ............... | A61N 1/06 607/122 |
| 5,824,026 A * | 10/1998 | Diaz | ................. | A61N 1/056 600/373 |
| 6,143,013 A * | 11/2000 | Samson | .............. | A61M 25/005 604/264 |
| 6,165,169 A * | 12/2000 | Panescu | .............. | A61B 18/1492 606/1 |
| 6,837,886 B2 * | 1/2005 | Collins | .............. | A61B 18/1492 606/41 |
| 7,047,081 B2 * | 5/2006 | Kuzma | ................ | A61N 1/0529 607/115 |
| 7,271,363 B2 * | 9/2007 | Lee | .......................... | H05H 1/24 219/121.36 |
| RE41,334 E * | 5/2010 | Beatty | ................ | A61B 5/04085 600/374 |
| 7,967,818 B2 * | 6/2011 | Kennedy, II | ....... | A61B 18/1492 606/45 |
| 8,249,685 B2 * | 8/2012 | Falwell | .............. | A61B 18/1492 600/373 |
| 8,721,677 B1 * | 5/2014 | Janardhan | ................. | A61F 2/01 606/200 |
| 2005/0065508 A1 * | 3/2005 | Johnson | ............... | A61B 5/0422 606/41 |
| 2012/0290067 A1 * | 11/2012 | Cam | ................ | A61B 17/12118 623/1.12 |

* cited by examiner

DIRECTIONAL MESH AND ASSOCIATED SYSTEMS

RELATED APPLICATIONS

This application claims the benefit of and priority to U.S. Provisional Application Ser. No. 61/752,314, filed Jan. 14, 2013, the contents of which are hereby incorporated by reference as if recited in full herein for all purposes.

BACKGROUND

The innovations and related subject matter disclosed herein (collectively referred to as the "disclosure") generally pertain to woven structures and associated systems for weaving such structures. Some aspects of disclosed innovations pertain to braided structures, such as braided wire structures, with a braided directional mesh being but one example. Other aspects of innovations disclosed herein pertain to methods of manufacturing woven structures, with an automated method of braiding a directional mesh being but one example. As but one example, some disclosed directional mesh structures constitute a portion of an energizable electrode configured for an electrosurgical therapy.

Figure 1A:
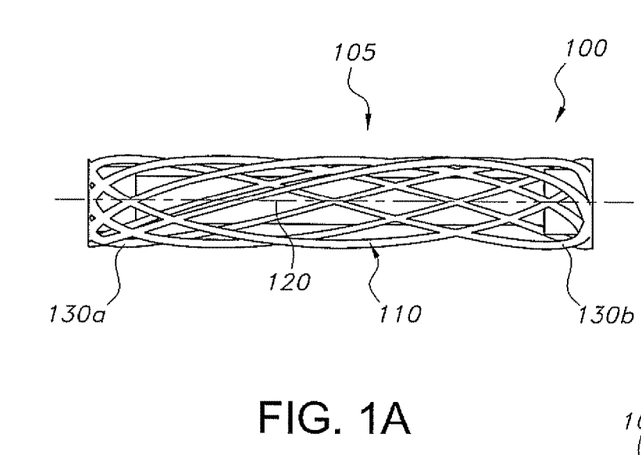
FIGS. 1A, 1B and 1C form a sequence of drawings showing a working embodiment of a directional mesh.
Figure 1B:
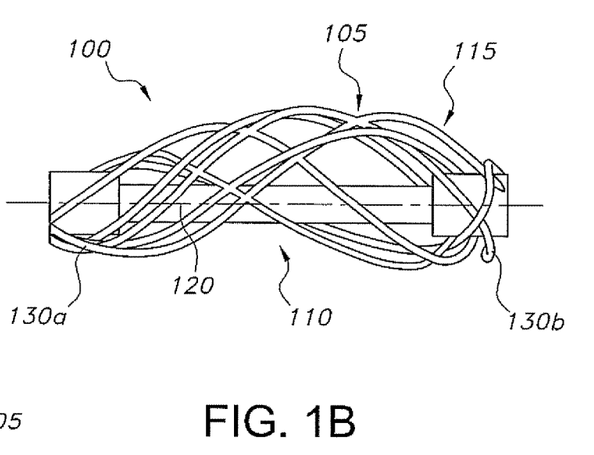
Figure 1C:
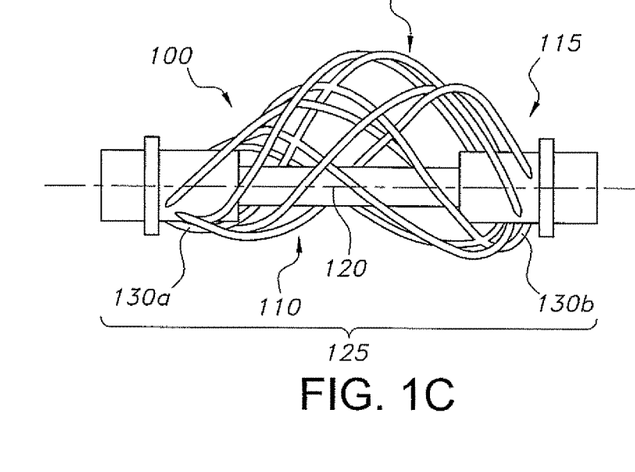

As used herein, the term "directional mesh" means an axially asymmetric woven structure. The sequence of drawings in FIGS. 1A, 1B and 1C shows a working embodiment of an innovative directional mesh.

Transurethral resection of the prostate (TURP) has been considered the reference 'gold standard' surgical procedure for low urinary tract symptoms (LUTS) due to benign prostatic hyperplasia (BPH). The high success rate of TURP as measured by substantial and sustained improvements of symptom scores, urinary flow rate and other functional parameters, remains associated with significant morbidity.

As a consequence, a number of minimally invasive therapeutic alternatives have been proposed during the last 30 years, including, inter alia, bipolar vaporization. Bipolar vaporization has shown promise as being an effective, safe and low-cost minimally invasive technique, providing very good hemostasis control and low complication rates. Suitable surgeon vision and hemostasis available during a bipolar vaporization procedure makes bipolar vaporization suitable for use in patients from high-risk groups, including those with cardiac pacemakers, bleeding disorders, or under anticoagulant therapy. Together with a relatively lower-cost per procedure compared to laser techniques, such advantages make bipolar vaporization an attractive technique for use in a variety of urological practice settings.

Bipolar vaporization techniques generate little heating of tissue surrounding a treatment site and are conducted without direct contact to tissue at a treatment site. In general, a bipolar electrode generates a thin plasma layer surrounding an electrically conductive portion of the electrode when an electrical current passes through the conductive portion. The plasma can vaporize a relatively thin layer of tissue at a treatment site on or in a patient's body without excessive heating (or other detrimental effect) of surrounding tissue.

To date, energizable electrodes have not allowed adjustments to their configuration during use. Nonetheless, an energizable electrode having an adjustable configuration can provide a surgeon with a variety of therapeutic options without having to replace or substitute one energizable electrode for another electrode having a different configuration.

Accordingly, there remains a need for an energizable electrode having an adjustable configuration. For example, there remains a need for an energizable electrode having a very compact profile to ease deployment of the electrode to a treatment site, being configured to expand to cover a relatively large area when deployed at or near the treatment site, and being further configured to contract to the compact profile for removal from the treatment site.

SUMMARY

The innovations disclosed herein overcome many problems in the prior art and address the aforementioned as well as other needs. By way of example, woven structures and associated systems for weaving such structures are disclosed. Some disclosed innovations pertain to braided structures, such as braided wire structures, with axially asymmetric woven structures (or "directional meshes") being examples. Other innovations disclosed herein pertain to methods of manufacturing woven structures, with automated methods of braiding directional meshes being examples. Some directional mesh embodiments can be configured and used as energizable electrodes for electrosurgical therapies, for example, bipolar vaporization therapies.

According to a first innovative aspect, woven constructs are disclosed. A woven construct can include a plurality of interwoven wires defining an operative segment. The operative segment can have a longitudinal axis. Positioned radially outwardly of the longitudinal axis, the operative segment can have a region of relatively higher wire-density and a region of relatively lower density. The operative segment can be a braided directional mesh.

In some embodiments, the region of relatively higher wire-density and the region of relatively lower wire-density are asymmetrically positioned relative to the longitudinal axis. Such a configuration can allow the operative segment to buckle in a predetermined direction under a sufficient, longitudinally compressive load applied to the operative segment. As but one example, the predetermined direction can be substantially radially outward relative to the longitudinal axis.

In some embodiments the plurality of wires can also define opposed end portions, with the operative segment being positioned between the opposed end portions. A wire-pitch of the operative segment can be substantially lower than a wire-pitch of one or both of the opposed end portions.

Each of the wires can extend substantially helically around the longitudinal axis by between about 120 degrees and about 240 degrees, such as, for example, by between about 150 degrees and about 210 degrees.

The operative segment can be configured to generate a suitable plasma field for an electrosurgical therapy when a sufficient electrical current passes through the plurality of interwoven wires.

According to another aspect, braiding machines are disclosed. For example, a braiding machine can be configured to so interweave a plurality of wires as to define a braided directional mesh.

Such a braiding machine can be configured to vary a longitudinal pitch of the interwoven wires. For example, a first segment of the braided directional mesh can have a corresponding first longitudinal pitch and a second segment of the braided directional mesh can have a corresponding second longitudinal pitch being relatively higher than the first longitudinal pitch.

In some embodiments, a braiding machine can have a first plurality of wire carriers configured to orbit about a portion of the braiding machine in a first orbital direction, and a second plurality of wire carriers configured to orbit about the portion of the braiding machine in a second orbital direction generally opposite to the first orbital direction. Such a braiding machine can also be configured to interweave each wire carrier in the first plurality of wire carriers with each wire carrier in the second plurality of wire carriers to interweave the plurality of wires.

In a general sense, the first plurality of wire carriers can include n wire carriers, and the second plurality of wire carriers can include m wire carriers. At least one and fewer than all of the n wire carriers can be populated with a supply of wire. At least one and fewer than all of the m wire carriers can be populated with a supply of wire. Such a braiding machine configuration can asymmetrically interweave the plurality of wires.

In some embodiments, the supply of wire can include a bobbin containing a corresponding spool of wire, and the corresponding plurality of spools of wire can constitute the plurality of wires.

According to yet another aspect, methods of forming a directional mesh are disclosed. For example, such a method can include axially asymmetrically interweaving each of a first plurality of wires with each of a second plurality of wires.

According to some disclosed methods, the first plurality of wires can be substantially helically wound in a first direction around a longitudinal axis, and the second plurality of wires can be substantially helically wound in a second direction around the longitudinal axis. A circumferential component of the first direction relative to the longitudinal axis can be substantially opposite a circumferential component of the second direction relative to the longitudinal axis. A longitudinal component of the first direction relative to the longitudinal axis can be substantially identical to a longitudinal component of the second direction relative to the longitudinal axis.

According to some disclosed methods, a region of relatively higher wire-density can circumferentially oppose, relative to the longitudinal axis, a region of relatively lower wire density. The region of relatively higher wire-density and the region of relatively lower wire-density can be configured such that the woven first and second pluralities of wires are configured to buckle in a predetermined direction under a sufficient, longitudinally compressive load.

According to some disclosed methods, an operative segment can be formed between opposed end segments. The operative segment can have a relatively lower pitch than either of the opposed end segments. In the operative segment, each of the plurality of wires can extend substantially helically around the longitudinal axis by between about 120 degrees and about 240 degrees, with between about 150 degrees and about 210 degrees being but one example of a suitable range of winding.

According to some disclosed methods, a directional mesh can be configured to generate a suitable plasma field for an electrosurgical therapy when a sufficient electrical current passes through the plurality of interwoven wires.

According to some disclosed methods, a longitudinal pitch of the interwoven wires can be varied. For example, a first segment of the directional mesh can have a corresponding first longitudinal pitch, and a second segment of the directional mesh can have a corresponding second longitudinal pitch being relatively higher than the first longitudinal pitch.

According to some methods, the act of interweaving each of the first plurality of wires with each of the second plurality of wires can include orbiting a first plurality of wire carriers about an orbital center in a first orbital direction and orbiting a second plurality of wire carriers about the orbital center in a second orbital direction. The second orbital direction can be in a direction generally opposite to the first orbital direction.

According to some methods, the first plurality of wire carriers can include n wire carriers and the second plurality of wire carriers can include m wire carriers. At least one and fewer than all of the n wire carriers can be populated. At least one and fewer than all of the m wire carriers can be populated. Each populated wire carrier can include a bobbin containing a corresponding spool of wire. A given plurality of spools of wire can constitute a respective plurality of wires.

The foregoing is not intended to be an exhaustive list of embodiments and features of the inventive subject matter. The appended claims, as originally filed in this document, or as subsequently amended, are hereby incorporated into this Summary section as if written directly in. Persons skilled in the art are capable of appreciating other embodiments and features from the following detailed description in conjunction with the drawings.

BRIEF DESCRIPTION OF THE DRAWINGS

Unless specified otherwise, the accompanying drawings illustrate aspects of the innovative subject matter described herein.

FIGS. 6A and 6B are drawings of a working embodiment of a braiding machine as described herein.

DETAILED DESCRIPTION

The following describes various principles related to woven structures and associated systems by way of reference to specific examples of braided structures and associated systems. In some innovative embodiments, a directional mesh constitutes a portion of an energizable electrode configured for electrosurgical therapy.

One or more of the principles can be incorporated in various system configurations to achieve any of a variety of system characteristics. Systems described in relation to particular configurations, applications, or uses, are merely examples of systems incorporating the innovative principles disclosed herein and are used to illustrate one or more innovative aspects of the disclosed principles. Accordingly, woven structures and associated systems having attributes differing from those specific examples discussed herein can embody one or more of the innovative principles. Accordingly, such alternative embodiments also fall within the scope and spirit of this disclosure.

Overview

An innovative woven structure can have an axial asymmetry or other characteristic adapted to cause the structure to buckle asymmetrically when sufficiently compressed axially. The sequence of drawings shown in FIGS. 1A, 1B and 1C illustrate a specific example of asymmetric buckling of a braided wire mesh.

As shown in FIG. 1A, the undeformed mesh 100 is axially asymmetric, having a region 105 of relatively higher wire density positioned circumferentially opposite a region 110 of relatively lower wire density. When longitudinally axially compressed sufficiently to buckle, the mesh 100 expands in a circumferentially asymmetric manner to form a bulge 115 extending radially outwardly of the longitudinal axis 120. Such a mesh is sometimes referred to as having a "directional" property insofar as the mesh 100 expands in generally one direction, as opposed to a circumferentially symmetric mesh that would tend to expand uniformly relative to the circumference, e.g., radially outward in all directions.

The directional mesh shown in FIGS. 1A, 1B, and 1C is configured as an energizable, bipolar electrode suitable for use in providing an electrosurgical therapy. The pictured directional mesh defines an operative segment 125 of the energizable electrode and is configured to extend between and electrically couple with opposed electrodes 130a, b. The opposed electrodes, in turn, are configured to urge toward each other and thereby apply a longitudinally compressive load to the operative segment 125. Such an electrode configuration can permit a surgeon to tailor the electrode configuration in situ to suit a given therapy without having to withdraw the electrode from a treatment site.

In some embodiments, a catheter or other electrosurgical device used in combination with disclosed energizable electrodes can be configured to limit the extent of longitudinal compressive or tensile displacement. Such a configuration can help ensure that the maximum stress within the energizable electrode remains sufficiently below the respective material's yield strength.

Woven Constructs

Figures 2, 3:
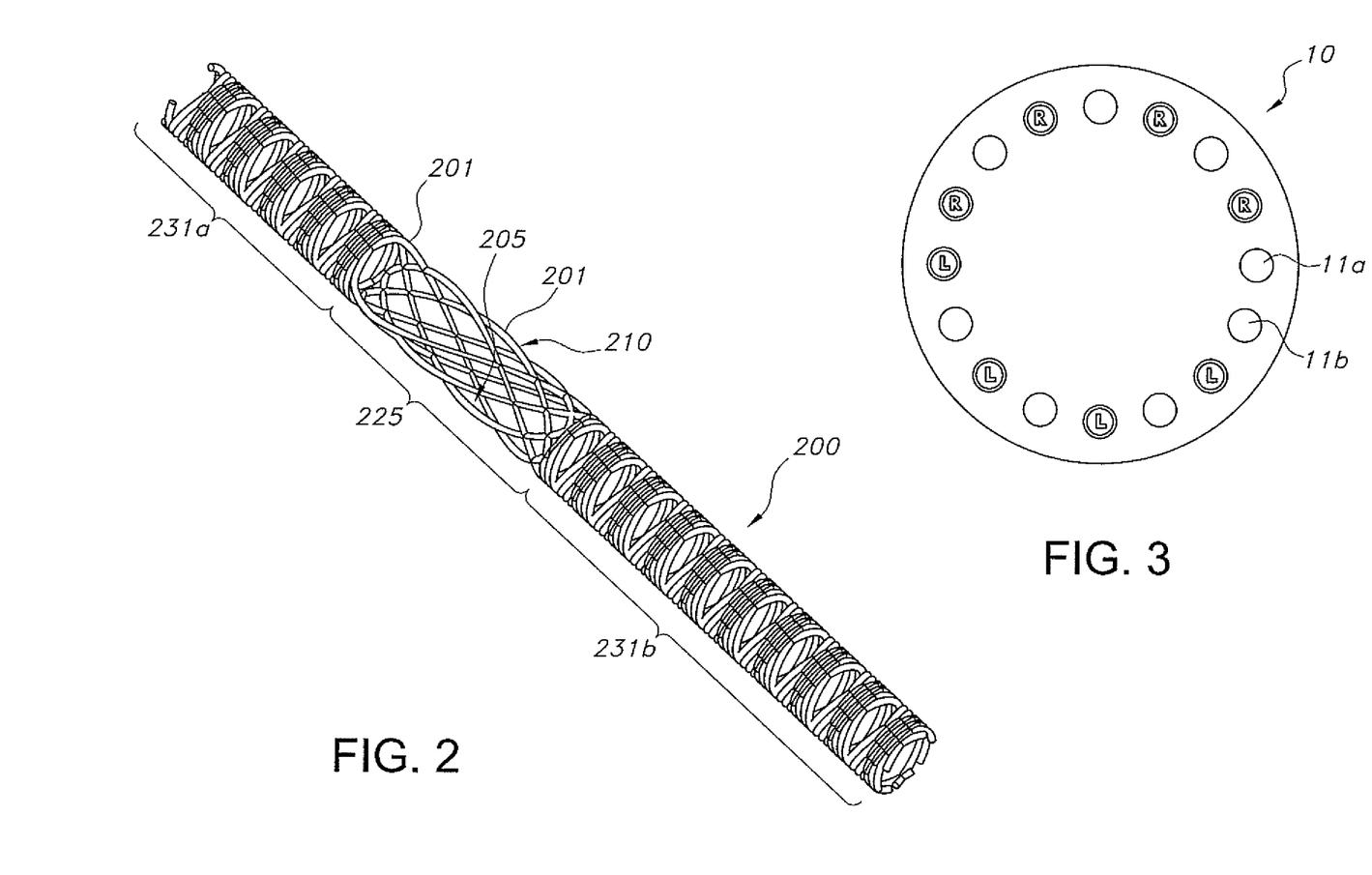
FIG. 2 shows an isometric view of an example of a woven structure of the type disclosed herein.
FIG. 3 shows a schematic illustration of a braiding machine configuration suitable for manufacturing a directional mesh.

As shown in FIG. 2, a woven construct 200 can be formed from a plurality of interwoven, biocompatible, electrically conductive wires 201 defining an operative segment 225 positioned between opposed end segments 231a, b. The operative segment 225 has a longitudinal axis (not shown). Positioned radially outwardly of the longitudinal axis, the operative segment 225 defines a region 205 of relatively higher wire-density and a region 210 of relatively lower density, similar to the working embodiment 100 pictured in FIGS. 1A, 1B, and 1C.

Some disclosed energizable electrodes can be formed from a material having a relatively high yield strength to permit the energizable electrode to change configurations without undergoing a plastic deformation. For example, some suitable materials can elastically deform between a compact configuration suitable for deploying the electrode (e.g., shown in FIG. 1A) and an expanded configuration (e.g., shown in FIG. 1C) suitable for electrosurgical therapies.

As but several examples, suitable materials for innovative electrosurgical electrodes can include an alloy of stainless steel, copper beryllium or platinum iridium. In some embodiments, a suitable wire can have a diameter of between about 0.005 inch and about 0.007 inch (inclusive). Well-suited materials for electrosurgical applications exhibit durability under repetitive cycles of energization and de-energization with RF electrical energy. As but one particular, but not exclusive, example, platinum can be well-suited for electrosurgical applications.

For applications that do not require electrical energization, high-strength polymer materials can be suitable. As an example, Kevlar can be a suitable material.

The region 205 of relatively higher wire-density and the region 210 of relatively lower wire-density are asymmetrically positioned relative to the longitudinal axis. Such a configuration permits the operative segment 225 to buckle in a predetermined direction under a sufficient, longitudinally compressive load applied to the operative segment. As shown in the sequence of drawings in FIGS. 1A, 1B, and 1C, the predetermined direction can be substantially radially outward relative to the longitudinal axis (e.g., axis 120).

As shown in FIG. 2, a wire-pitch of the operative segment 225 is substantially lower than a wire-pitch of one or both of the opposed end portions 231a, b. As used herein, "wire-pitch" refers to a ratio of a measure of a given wire's circumferential winding to a measure of length. In some instances, the measure of length can be measured relative to the resulting construct (e.g., a directional mesh 100, 200) and in other instances the measure of length can be measured relative to the wire (e.g., a length of the wire 201). As but one example, a given wire-pitch of a wire extending about half-way around a longitudinal axis in one centimeter could be 0.5 windings per centimeter. Another, relatively higher wire-pitch could be 2 windings per centimeter.

In a general sense, regions of a woven construct 200 outside the operative segment 225 can be woven to a suitably high pitch (e.g., approaching a "solid tubular" construct). As but one example, a 0.041 inch mandrel was used to weave a 0.005 inch diameter wire at a pitch of about 130 windings per inch (PPI) (e.g., between about 120 PPI and about 140 PPI) for regions outside of the operative segment 225. In contrast, the operative segment 225 was woven at about 1-3 PPI over a distance of between about 0.3 inch to about 0.4 inch. A woven construct 200 can include a plurality of operative segments 225 juxtaposed with a corresponding plurality of outside regions 231a, b. Each outside region 231a, b of the woven construct 200 can be cut to separate individual energizable electrodes from the woven construct 200. The outside regions 231a, b can be trimmed to a selected length.

As shown in FIG. 2, each of the wires 201 extends substantially helically around the longitudinal axis, though each wire is interwoven with several other wires causing the wires to depart slightly from a pure helical winding. In the operative segment 225, the wires extend circumferentially around the longitudinal axis by about 180 degrees, for example between about 120 degrees and about 240 degrees, such as between about 150 degrees and about 210 degrees. Stated differently, a distal end of a given helical wire 201 in the operative segment 225 is circumferentially offset from the corresponding proximal end by about 180 degrees, for example between about 120 degrees and about 240 degrees, such as between about 150 degrees and about 210 degrees.

Interweaving

A directional mesh can be formed by axially asymmetrically interweaving each of a first plurality of wires 201 with each of a second plurality of wires 201.

For example, as shown schematically in the sequence of illustrations in FIGS. 4A, 4B, 4C and 4D, a braiding machine 10 can interweave each of a first plurality of wires (or wire carriers, for example, bobbins having respective spools of wire) 13a with each of a second plurality of wires (or wire carriers, for example, bobbins having respective spools of wire) 13b. In particular, the braiding machine 10 has a platen 11 having a bi-directional track 12a, 12b configured to urge the first plurality of wires 13a generally clockwise through a nominal orbit 16 relative to the platen 11 and to urge the second plurality of wires 13b generally counter-clockwise through the nominal orbit 16.

Figure 4A:
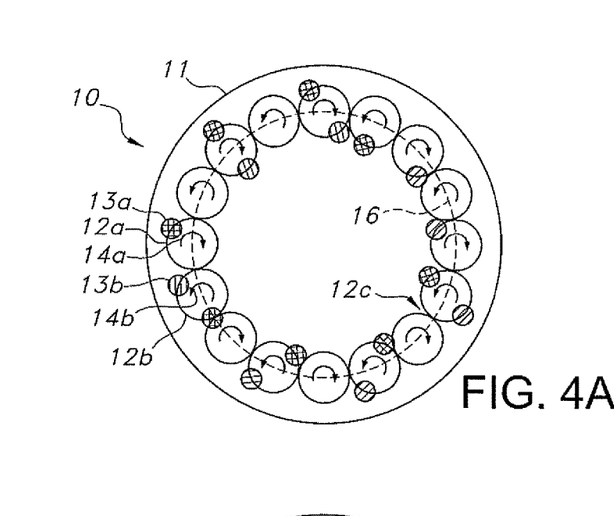
FIGS. 4A, 4B, 4C and 4D schematically illustrate a sequence of braiding machine configurations during a braiding process.
Figure 4B:
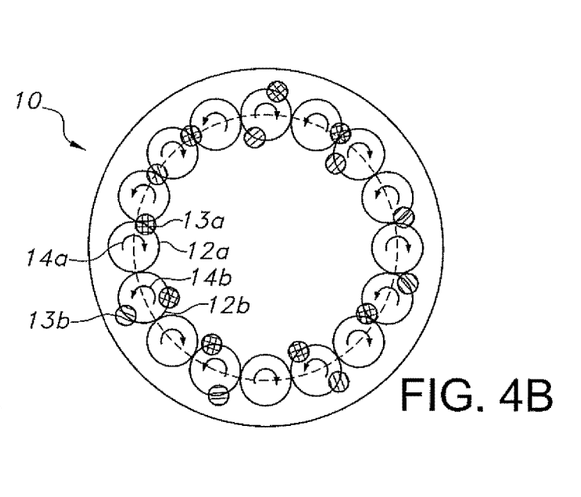
Figure 4C:
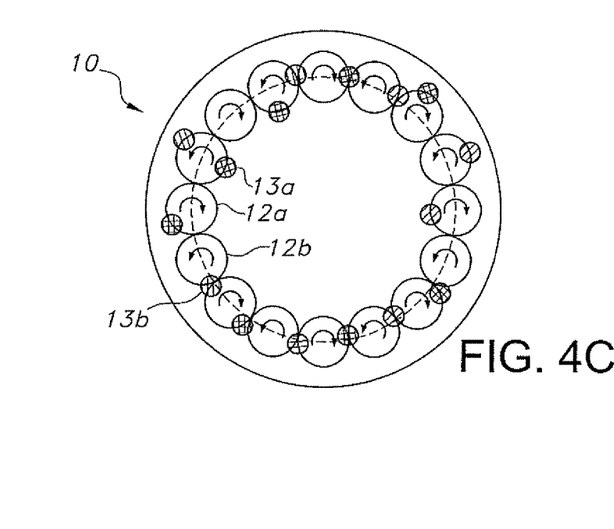
Figure 4D:
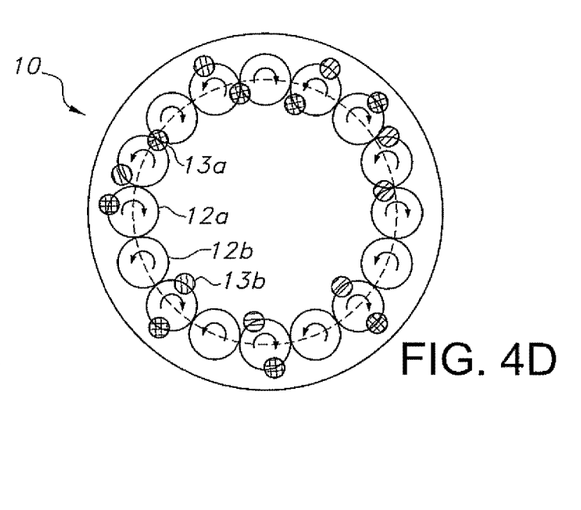
Figure 5A:
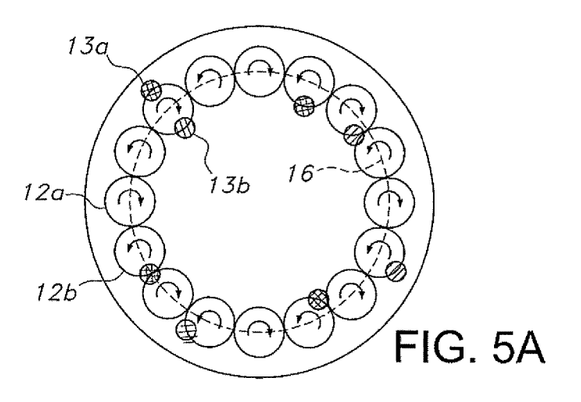
FIGS. 5A, 5B, 5C and 5D schematically illustrate a sequence of braiding machine configurations during a directional mesh braiding process.
Figure 5B:
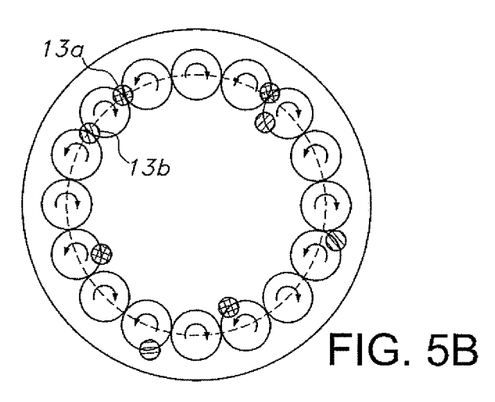
Figure 5C:
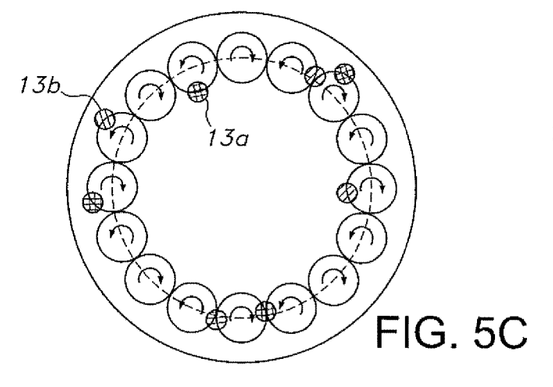
Figure 5D:
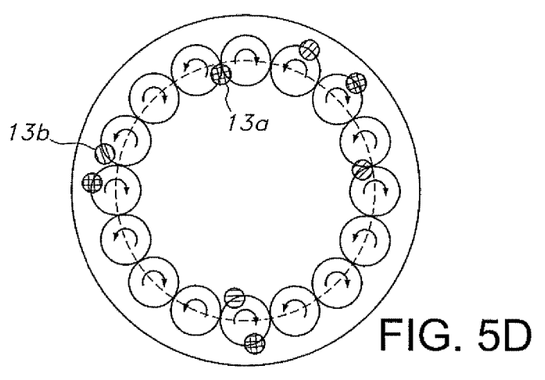
Figure 6A:
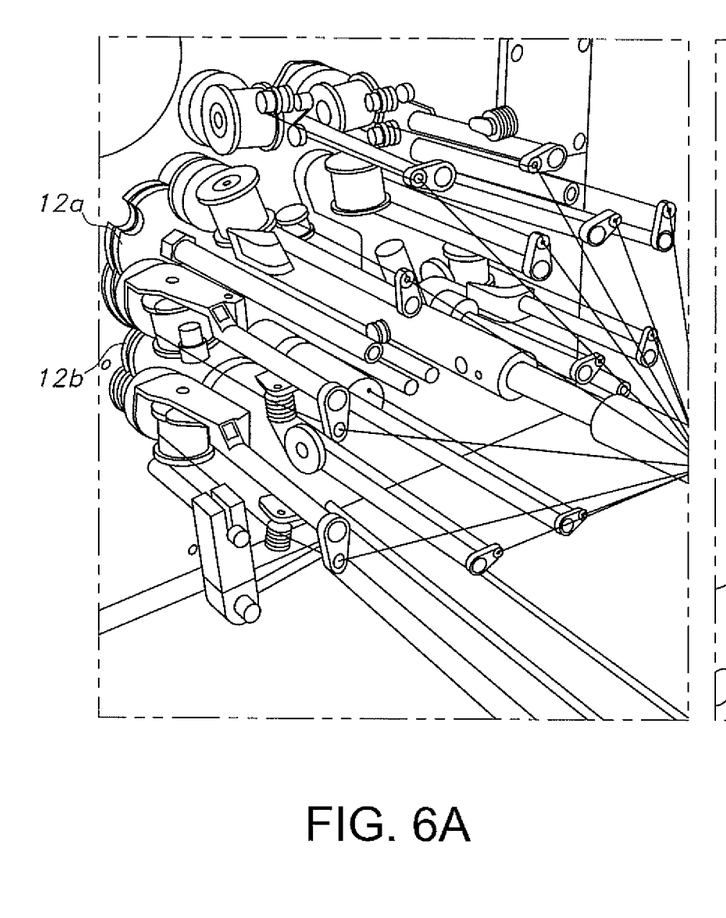
Figure 6B:
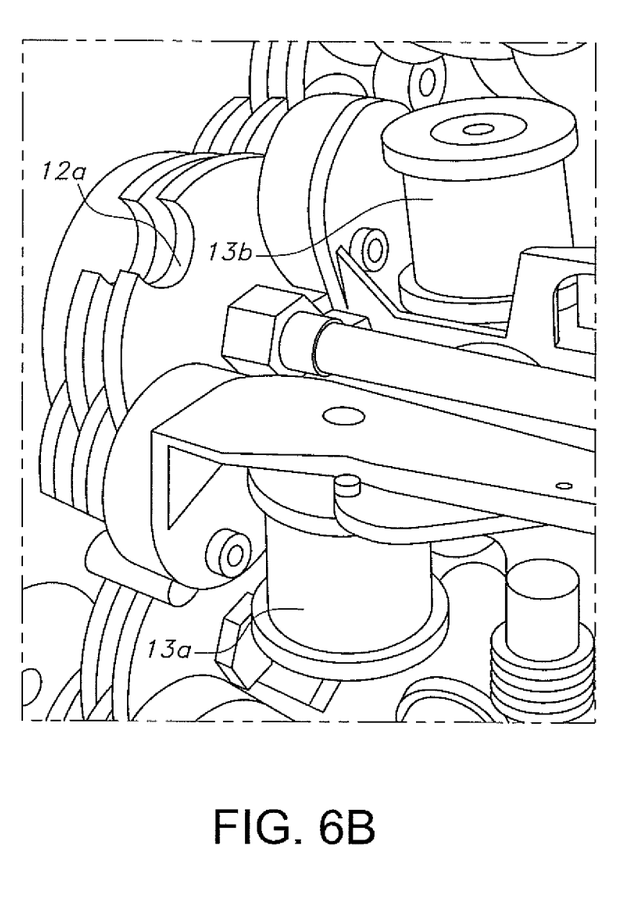
FIG. 6B shows a carrier populated with a bobbing having a spool of wire.
Figure 7:
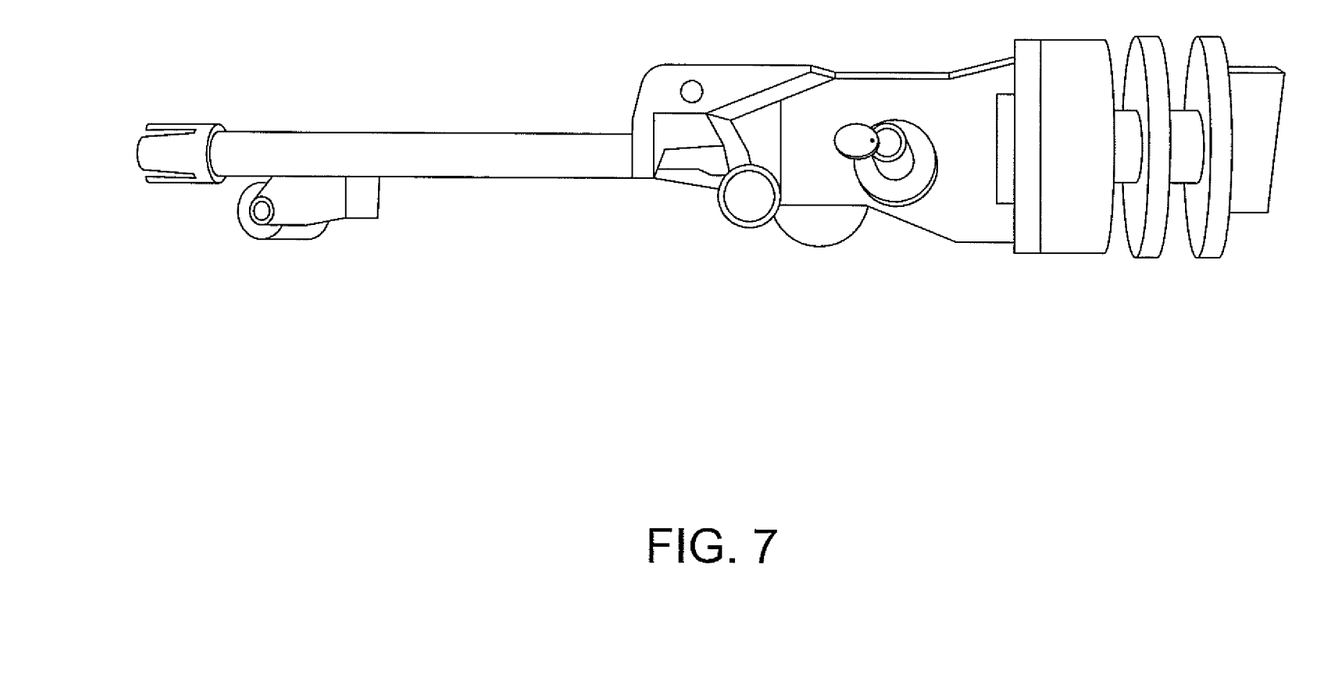
FIG. 7 is a drawing of an unpopulated carrier separate from and suitable for use with a braiding machine as shown in FIG. 6A.

In the example shown in FIGS. 4A, 4B, 4C and 4D, the orbital paths defined by the tracks 12a, 12b oscillate radially relative to the platen 11 about the nominal orbit 16. The tracks 12a and 12b intersect at, for example, intersection 12c. The bi-directional track 12a, 12b causes the wires 13a to interweave with the wires 13b as the wires 13a, 13b travel through their respective orbital paths. Motions of the wires 13a, 13b along each portion of the tracks 12a, 12b are indicated by the arrows 14a, 14b. FIG. 4B shows an intermediate configuration of a braiding machine 10, as well as relative positions of first and second pluralities of wires 13a, 13b, after each rotatable portion of the bi-directional track 12a, 12b has advanced by about 90 degrees relative to the position shown in FIG. 4A. FIG. 4C shows the braiding machine 10 and wires 13a, 13b after the bi-directional track 12a, 12b has advanced by about 90 degrees relative to the position shown in FIG. 4B. FIG. 4D shows the braiding machine 10 and wires 13a, 13b after the bi-directional track 12a, 12b has advanced by about 90 degrees relative to the position shown in FIG. 4C. As the wires 13a, 13b pass through their respective counter-directional orbits, the interweaving of the wires 13a, 13b forms a woven construct adjacent an orbital center, similar to woven ribbons wound about a maypole.

As noted above in relation to FIGS. 4A, 4B, 4C and 4D, some braiding machines 10 interweave first and second pluralities of spools of wire 13a, 13b. More particularly, some braiding machines 10 are configured to withdraw a woven construct from the orbital center of the platen 11 (e.g., in a direction generally perpendicular to the platen 11).

Wire-pitch of a woven construct formed using an approach as summarized above is proportional to orbital speed (e.g., number of orbits per unit of time) of the wires (or carriers) 13a, 13b and inversely proportional to a speed at which the woven construct is withdrawn, e.g., from the braiding machine. Accordingly, if a rate at which the woven construct is withdrawn increases and the orbital speed of the wires 13a, 13b remains constant, the resulting construct will have a relatively lower wire-pitch. Conversely, if a rate at which the woven construct is withdrawn decreases and the orbital speed of the wires 13a, 13b remains constant, the resulting construct will have a relatively higher wire-pitch. Thus, the construct shown in FIG. 2 can be formed by withdrawing the construct at a relatively lower rate while the end segments 231a, b are being woven, and withdrawing the construct at a relatively higher rate while the operative segment 225 is being woven.

The mesh design and the set-up of the braider to produce the design enable the directional mesh shown in FIGS. 1A-C and 2 to be made in a continuous process on a multi-carrier braiding machine as depicted in FIGS. 4A-D, 5A-D and 6. For example, a continuous woven construct can comprise a plurality of operative segments 225 juxtaposed with a plurality of end segments 231a, b. The continuous woven construct can be segmented (e.g., each end segment 231a, b can be bisected to form one woven construct 200 having an operative segment 225 positioned between opposed end segments 231a, b, as shown in FIG. 2.)

Withdrawing a woven construct formed from the orbiting wires (or carriers) 13a, 13b can cause the first plurality of wires 13a to be substantially helically wound in a first direction around a longitudinal axis, and the second plurality of wires to be substantially helically wound in a second direction around the longitudinal axis. With the counter-orbits described above, a circumferential component of the first direction relative to the longitudinal axis is substantially opposite a circumferential component of the second direction relative to the longitudinal axis, while a longitudinal component of the first direction relative to the longitudinal axis is substantially identical to a longitudinal component of the second direction relative to the longitudinal axis.

An asymmetrically loaded braiding machine 10, as shown in FIGS. 5A-D can interweave a plurality of wires to define a braided directional mesh of the type shown in FIGS. 1A, 1B, 1C, 1d and 2. In particular, operating an asymmetrically loaded braiding machine can form a woven construct having a region of relatively higher wire-density circumferentially opposing, relative to a longitudinal axis, a region of relatively lower wire density.

For example, as shown in FIGS. 3, 4A, 4B, 4C, and 4D, a braiding machine 10 can have 16 wire carriers, with 8 wire carriers configured to orbit generally in a clockwise direction relative to the platen 11 and 8 wire carriers configured to orbit generally in a counter-clockwise direction relative to the platen 11. In FIGS. 3 and 5A, 5B, 5C and 5D, fewer than all available wire carriers (and at least one carrier corresponding to each orbital direction) populate the platen 11 asymmetrically.

For example, in FIG. 3, several populated wire carriers, R, configured to orbit in a generally clockwise direction relative to the platen 11 are juxtaposed with unpopulated wire carriers configured to orbit in the same direction. Similarly, several populated wire carriers, L, configured to orbit in a generally counter-clockwise direction relative to the platen 11 are juxtaposed with unpopulated wire carriers configured to orbit in the same direction. The asymmetry is introduced insofar as a populated carrier R is positioned adjacent a populated carrier L, and counter-orbiting, unpopulated carriers 11a, b are positioned adjacent to each other. Such an asymmetric loading of a braiding machine can form a directional mesh construct as shown in FIGS. 1A, 1B, 1C and 2.

Although 16-carrier braiding machines have been described by way of example, above, similar principles apply to any braiding machine having a first plurality of wire carriers configured to interweave with a counter-orbiting second plurality of wire carriers. For example, the first plurality of wire carriers can include n wire carriers and the second plurality of wire carriers can include m wire carriers. At least one and fewer than all of the n wire carriers can be populated, and at least one and fewer than all of the m wire carriers can be populated, and the braiding machine can thereby be configured to asymmetrically interweave the first plurality of wire carriers with the second plurality of wire carriers to form a directional mesh.

Other Exemplary Embodiments

The embodiments described above generally concern woven structures configured to buckle in a predetermined direction. Nonetheless, other embodiments are possible. For example, a coil spring can be bowed outwardly. Such a coil spring can, in some embodiments, have a longitudinally variable coil pitch (e.g., a segment of the spring can be plastically deformed, or "stretched," to impart the segment with a relatively lower pitch). A region of relatively lower pitch can be urged together to bow outwardly. In another alternative embodiment, one or more apertures can be cut into a tubular metal structure (e.g., by laser cutting), defining a segment of the tubular metal structure configured to buckle in a predetermined direction under a longitudinally compressive load.

This disclosure references the accompanying drawings, which form a part hereof, wherein like numerals designate like parts throughout. The drawings illustrate specific embodiments, but other embodiments may be formed and structural and logical changes may be made without departing from the intended scope of this disclosure.

Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" or "or", as well as "and" and "or."

All patent and non-patent literature cited herein is hereby incorporated by references in its entirety for all purposes. Incorporating the principles disclosed herein, it is possible to provide a wide variety of systems configured to render an electrosurgical handpiece inoperable at or near an end of the handpiece's safe useful life, in addition to the systems described above.

The technologies from any example can be combined with the technologies described in any one or more of the other examples. Accordingly, this detailed description shall not be construed in a limiting sense, and following a review of this disclosure, those of ordinary skill in the art will appreciate the wide variety of electrosurgical systems that can be devised using the various concepts described herein. Moreover, those of ordinary skill in the art will appreciate that the exemplary embodiments disclosed herein can be adapted to various configurations without departing from the disclosed principles. Thus, in view of the many possible embodiments to which the disclosed principles can be applied, it should be recognized that the above-described embodiments are only examples and should not be taken as limiting in scope. Therefore, I claim all that comes within the scope and spirit of the following claims, and reserve the right to claim in the future any or all aspects of any innovation shown or described herein.

I currently claim:

1. A woven construct, consisting of:
a) a first plurality of wires interwoven with a second plurality of wires, wherein the first plurality of wires are woven in a first helical direction at a pitch of from about 120° to about 240° and the second plurality of wires are woven in a second, opposite helical direction at a pitch of from about 120° to about 240° about a longitudinal axis to thereby provide the first and second plurality of wires being interwoven and extending from a proximal interwoven end segment to a spaced apart distal interwoven end segment, wherein an operative segment resides intermediate the proximal and distal interwoven end segments,
b) wherein with respect to an imaginary plane aligned substantially perpendicular to the longitudinal axis, the first and second plurality of interwoven wires in the operative segment comprise a first region of relatively higher interwoven wire-density positioned circumferentially spaced from a second region of relatively lower interwoven wire-density, and
c) wherein the proximal and distal interwoven end segments have the same number of wires, each as a sum of the first and second plurality of interwoven wires, and wherein the combined first and second regions of relatively higher and lower interwoven wire-density have an equal number of wires as the sum of the first and second plurality of interwoven wires in the respective proximal and distal interwoven end segments, and
d) wherein in a compact configuration devoid of an axial force being applied to at least one of the proximal and distal interwoven end segments toward the other end segment, the woven construct of the first and second plurality of interwoven wires has a substantially cylindrical shape about and along the longitudinal axis, and
e) wherein the woven construct is configured so that upon the application of a compressive load being applied to at least one of the proximal and distal interwoven end segments, the operative segment is deformable into an asymmetrically-buckled configuration having the first region of relatively higher interwoven wire-density being spaced radially outwardly further from the longitudinal axis than the second region of relatively lower interwoven wire-density.

2. The woven construct according to claim 1, wherein the first region of relatively higher interwoven wire-density is positioned circumferentially opposite the second region of relatively lower interwoven wire-density.

3. The woven construct according to claim 1, wherein a first wire-pitch of one or both of the opposed proximal and distal interwoven end segments is greater than a second wire-pitch of the operative segment.

4. The woven construct according to claim 1, wherein each of the first and second plurality of interwoven wires extends substantially helically around the longitudinal axis at a pitch of from about 150° to about 210°.

5. The woven construct according to claim 1, wherein the operative segment is a braided directional mesh.

6. The woven construct according to claim 1, wherein, when an electrical current passes through the first and second plurality of interwoven wires, the operative segment is configured to generate a plasma field for an electrosurgical therapy.

7. The woven construct according to claim 1, wherein the asymmetrically-buckled configuration comprises the first region of relatively higher interwoven wire-density having deformed substantially radially outwardly relative to the longitudinal axis.

8. The woven construct according to claim 1, wherein the compressive load is a longitudinally compressive load.

9. The woven construct according to claim 1, wherein the first and second plurality of interwoven wires are of either an electrically conductive material or of a polymeric material.

10. A woven construct, consisting of:
a) a first plurality of electrically conductive wires interwoven with a second plurality of electrically conductive wires, wherein the first plurality of wires are woven in a first helical direction at a pitch of from about 120° to about 240° and the second plurality of wires are woven in a second, opposite helical direction at a pitch of from about 120° to about 240° about a longitudinal axis to thereby provide the first and second plurality of wires being interwoven and extending from a proximal interwoven end segment providing a first electrode to a spaced apart distal interwoven end segment providing a second electrode, wherein an operative segment resides intermediate the proximal and distal interwoven end segments, b) wherein with respect to an imaginary plane aligned substantially perpendicular to the longitudinal axis, the first and second plurality of interwoven wires in the operative segment comprise a first region of relatively higher interwoven wire-density positioned circumferentially spaced from a second region of relatively lower interwoven wire-density, c) wherein the proximal and distal interwoven end segments have the same number of interwoven wires, each as a sum of the first and second plurality of wires, and wherein the combined first and second regions of relatively higher and lower interwoven wire-density have an equal number of wires as the sum of the first and second plurality of interwoven wires in the respective proximal and distal interwoven end segments, d) wherein in a compact configuration devoid of an axial force being applied to at least one of the first and second electrodes toward the other electrode, the woven construct of the first and second plurality of interwoven wires has a substantially cylindrical shape about and along the longitudinal axis, and e) wherein the woven construct is configured so that upon the application of a compressive load being applied to at least one of the first and second electrodes, the operative segment is deformable into an asymmetrically-buckled configuration having the first region of relatively higher interwoven wire-density being spaced radially outwardly further from the longitudinal axis than the second region of relatively lower interwoven wire-density, and f) wherein, when an electrical current passes from the first electrode through the first and second plurality of interwoven wires in the operative segment and to the second electrode, the operative segment is configured to generate a plasma field for an electrosurgical therapy.

11. The woven construct of claim 10, wherein the first region of relatively higher interwoven wire-density and the second region of relatively lower interwoven wire-density are asymmetrically positioned relative to the longitudinal axis.

12. The woven construct of claim 10, wherein the asymmetrically-buckled configuration comprises the first region of relatively higher interwoven wire-density having deformed substantially radially outwardly relative to the longitudinal axis.

13. The woven construct of claim 10, wherein the first region of relatively higher interwoven wire-density is positioned circumferentially opposite the second region of relatively lower interwoven wire-density.

14. The woven construct of claim 10, wherein a first wire-pitch of one or both of the opposed proximal and distal interwoven end segments providing the respective first and second electrodes is greater than a second wire-pitch of the operative segment.

15. The woven construct of claim 10, wherein the pitch is from about 150° to about 210°.

16. The woven construct of claim 10, wherein the compressive load is a longitudinally compressive load.

17. A woven construct, consisting of:

a) a first plurality of wires of a polymeric material interwoven with a second plurality of wires of a polymeric material, wherein the first plurality of wires are woven in a first helical direction at a pitch of from about 120° to about 240° and the second plurality of wires are woven in a second, opposite helical direction at a pitch of from about 120° to about 240° about a longitudinal axis to thereby provide the first and second plurality of wires being interwoven and extending from a proximal interwoven end segment to a spaced apart distal interwoven end segment, wherein an operative segment resides intermediate the proximal and distal interwoven end segments, b) wherein with respect to an imaginary plane aligned substantially perpendicular to the longitudinal axis, the first and second plurality of interwoven wires in the operative segment comprise a first region of relatively higher interwoven wire-density positioned circumferentially spaced from a second region of relatively lower interwoven wire-density, c) wherein the proximal and distal interwoven end segments have the same number of wires, each as a sum of the first and second plurality of interwoven wires, and wherein the combined first and second regions of relatively higher and lower interwoven wire-density have an equal number of wires as the sum of the first and second plurality of interwoven wires in the respective proximal and distal interwoven end segments, d) wherein in a compact configuration devoid of an axial force being applied to at least one of the first and second end segments toward the other end segment, the woven construct of the first and second plurality of interwoven wires has a substantially cylindrical shape about and along the longitudinal axis, and e) wherein the woven construct is configured so that upon the application of a compressive load being applied to at least one of the first and second interwoven end segments, the operative segment is deformable into an asymmetrically-buckled configuration having the first region of relatively higher interwoven wire-density being spaced radially outwardly further from the longitudinal axis than the second region of relatively lower interwoven wire-density.

18. The woven construct of claim 17, wherein the first region of relatively higher interwoven wire-density and the second region of relatively lower interwoven wire-density are asymmetrically positioned relative to the longitudinal axis.

19. The woven construct of claim 17, wherein the asymmetrically-buckled configuration comprises the first region of relatively higher interwoven wire-density having deformed substantially radially outwardly relative to the longitudinal axis.

20. The woven construct of claim 17, wherein the first region of relatively higher interwoven wire-density is positioned circumferentially opposite the second region of relatively lower interwoven wire-density.

21. The woven construct of claim 17, wherein a first wire-pitch of one or both of the opposed proximal and distal interwoven end segments is greater than a second wire-pitch of the operative segment.

22. The woven construct of claim 17, wherein the pitch is from about 150° to about 210°.

23. The woven construct of claim 17, wherein the compressive load is a longitudinally compressive load.

* * * * *